United States Patent
Everett et al.

(10) Patent No.: US 11,395,589 B2
(45) Date of Patent: Jul. 26, 2022

(54) SYSTEMS AND METHODS FOR CHARACTERIZING REFRACTION WITH OPHTHALMIC IMAGING SYSTEMS

(71) Applicants: Carl Zeiss Meditec, Inc., Dublin, CA (US); Carl Zeiss Meditec AG, Jena (DE)

(72) Inventors: Matthew J. Everett, Livermore, CA (US); Alexandre R. Tumlinson, San Leandro, CA (US); David J. Nolan, Dublin, CA (US); Conor Leahy, Dublin, CA (US); Keith O'Hara, Pleasanton, CA (US)

(73) Assignees: CARL ZEISS MEDITEC, INC., Dublin, CA (US); CARL ZEISS MEDITEC AG, Jena (DE)

( * ) Notice: Subject to any disclaimer, the term of this patent is extended or adjusted under 35 U.S.C. 154(b) by 144 days.

(21) Appl. No.: 16/494,016

(22) PCT Filed: Mar. 29, 2018

(86) PCT No.: PCT/EP2018/058138
§ 371 (c)(1),
(2) Date: Sep. 13, 2019

(87) PCT Pub. No.: WO2018/178269
PCT Pub. Date: Oct. 4, 2018

(65) Prior Publication Data
US 2020/0085294 A1    Mar. 19, 2020

Related U.S. Application Data

(60) Provisional application No. 62/543,709, filed on Aug. 10, 2017, provisional application No. 62/479,786, filed on Mar. 31, 2017.

(51) Int. Cl.
*A61B 3/10* (2006.01)
*A61B 3/103* (2006.01)
(Continued)

(52) U.S. Cl.
CPC ............ *A61B 3/1025* (2013.01); *A61B 3/103* (2013.01); *A61B 3/12* (2013.01); *A61B 3/14* (2013.01)

(58) Field of Classification Search
CPC ......... A61B 3/1025; A61B 3/103; A61B 3/12; A61B 3/14
(Continued)

(56) References Cited

U.S. PATENT DOCUMENTS 3,925,793 A     12/1975  Matsumura et al.
4,162,828 A *   7/1979   Trachtman ............. A61B 3/103
                                             351/211

(Continued)

FOREIGN PATENT DOCUMENTS

WO    2000/19885 A1    4/2000
WO    2011/076943 A2   6/2011
WO    2012/059236 A1   5/2012

OTHER PUBLICATIONS

International Preliminary Report on Patentability received for PCT Patent Application No. PCT/EP2018/058138, dated Oct. 10, 2019, 8 pages.
(Continued)

*Primary Examiner* — Mohammed A Hasan
(74) *Attorney, Agent, or Firm* — Morrison & Foerster LLP

(57) ABSTRACT

Ophthalmic imaging systems, particularly slit-scanning ophthalmo-scopes, are capable of characterizing refraction over the entire field of view of the system. Light from the light source of the system illuminates a region of the eye and the
(Continued)

returning light is measured on a detector. The deviation of the location of the returning light from a predetermined location on the detector is measured. The deviation corresponds to the mismatch between the refractions of the imaging system and the eye. The light can be scanned across the full field of view to characterize the entire field. A second illumination source traveling along a second illumination path can be used to improve the characterization. The characterization can be of use for optimizing the focus of the instrument and for assessing the condition of the eye, including assessing myopia and astigmatism in the periphery.

24 Claims, 12 Drawing Sheets

(51) Int. Cl.
    *A61B 3/12*         (2006.01)
    *A61B 3/14*         (2006.01)

(58) Field of Classification Search
    USPC ............................................. 351/206
    See application file for complete search history.

(56) References Cited

U.S. PATENT DOCUMENTS

| | | | |
|---|---|---|---|
| 5,258,791 | A | 11/1993 | Penney et al. |
| 5,907,388 | A | 5/1999 | Fujieda |
| 9,078,602 | B2 | 7/2015 | Plaian et al. |
| 9,456,746 | B2 | 10/2016 | Bublitz et al. |
| 2005/0007551 | A1 | 1/2005 | Wakil et al. |
| 2007/0253688 | A1 | 11/2007 | Koennecke |
| 2015/0131050 | A1 | 5/2015 | Bublitz et al. |
| 2015/0374233 | A1* | 12/2015 | Zhang ............... A61B 3/14 351/206 |
| 2016/0120405 | A1 | 5/2016 | Tokuda et al. |

OTHER PUBLICATIONS

International Search Report and Written Opinion received for PCT Patent Application No. PCT/EP2018/058138, dated Jul. 6, 2018, 10 pages.

Jaeken et al., "Fast Scanning Peripheral Wave-front Sensor for the Human Eye", Optics Express, vol. 19, No. 8, Apr. 11, 2011, pp. 7903-7913.

Kerr, Douglas A., "Principle of the Split Image Focusing Aid and the Phase Comparison Autofocus Detector in Single Lens Reflex Cameras", The Pumkin, Retrieved from: http://dougkerr.net/Pumpkin/articles/Split_Prism.pdf, Aug. 27, 2005, pp. 1-17.

Ko, Dong-Seob, "Optics of Refractometers for Refractive Power Measurement of the Human Eye", Journal of the Optical Society of Korea, vol. 10, No. 4, Dec. 2006, pp. 145-156.

Osuagwu et al., "Peripheral Refraction Validity of the Shin-Nippon Srw5000 Autorefractor", Optometry and Vision Science, vol. 93, No. 10, 2016, pp. 1254-1261.

Tabernero et al., "Fast Scanning Photoretinoscope for Measuring Peripheral Refraction as a Function of Accommodation", Optical Society of America, vol. 26, No. 10, Oct. 2009, pp. 2206-2210.

Tabernero et al., "More Irregular Eye Shape in Low Myopia Than in Emmetropia", Invest Ophthalmol Vis Sci, vol. 50, No. 9, Sep. 2009, pp. 4516-4522.

Tabernero et al., "Peripheral Refraction Profiles in Subjects with Low Foveal Refractive Errors", Optometry and Vision Science, vol. 88, No. 3, 2011, pp. E388-E394.

* cited by examiner

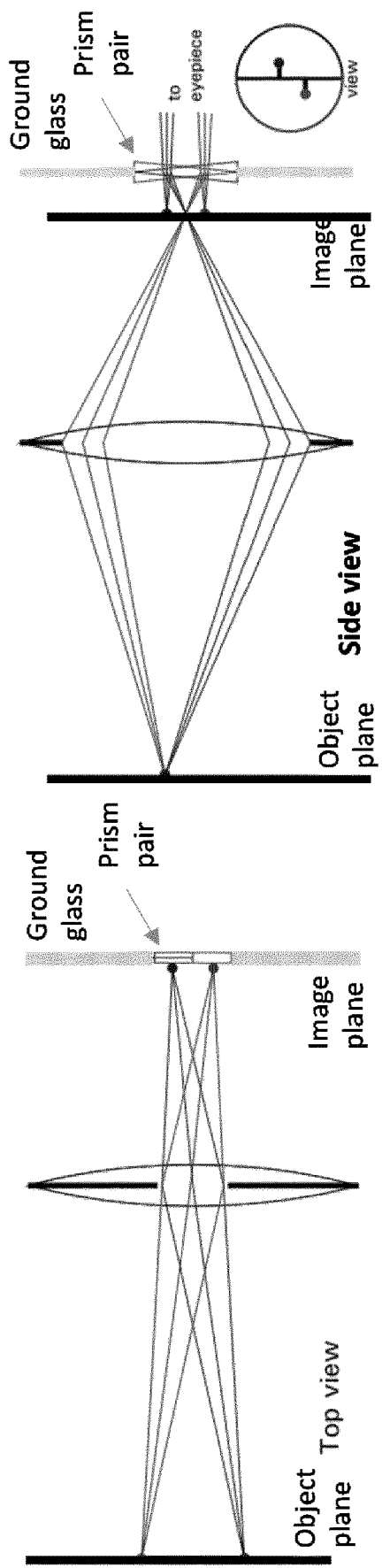

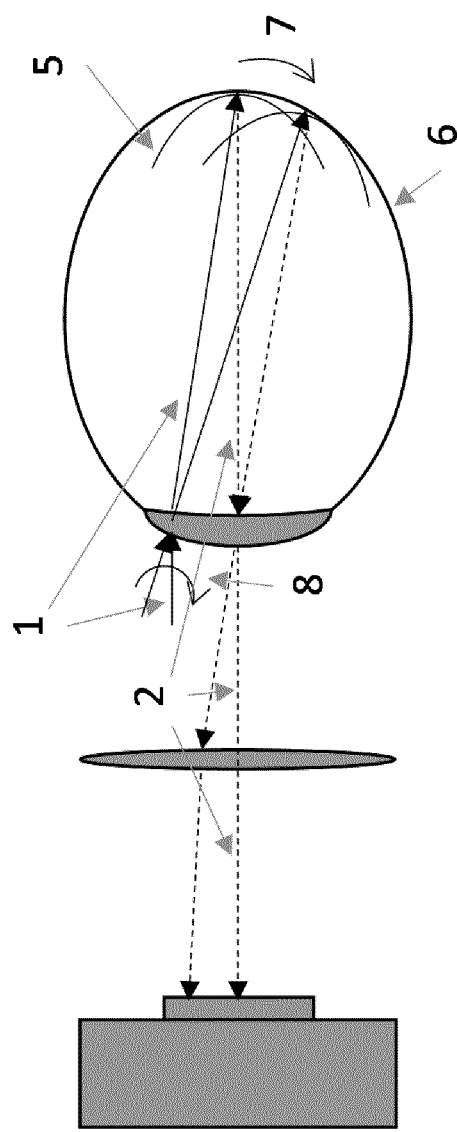
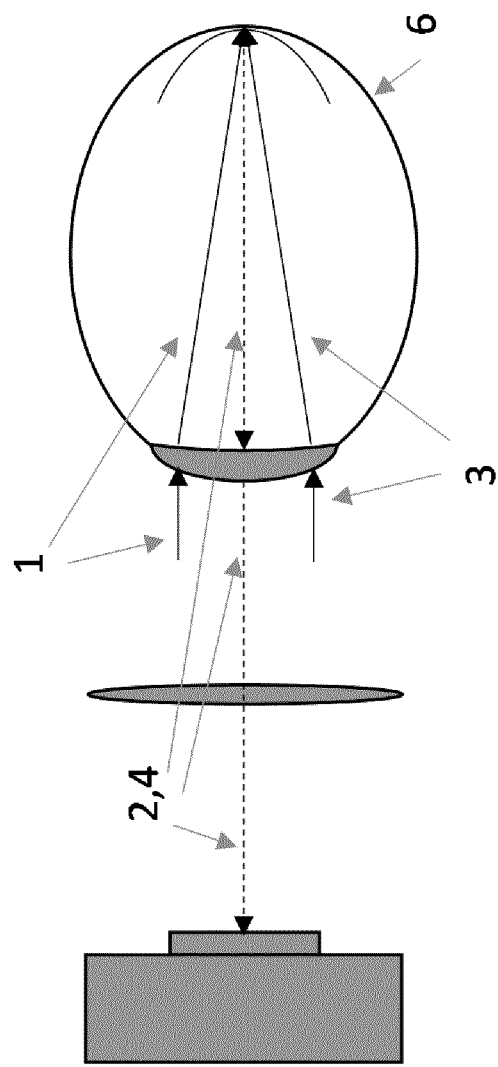
FIG. 2b
FIG. 2c

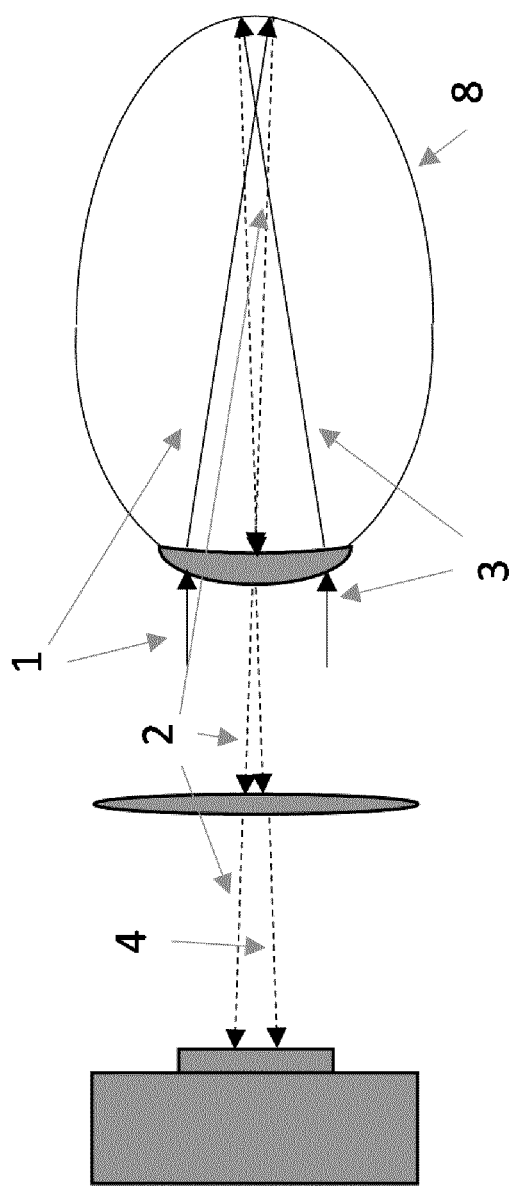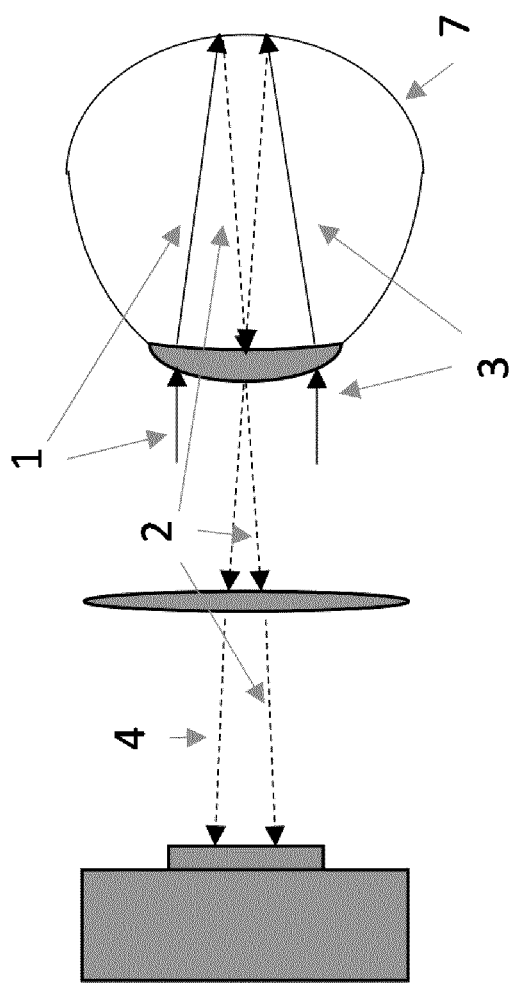
FIG. 2d
FIG. 2e

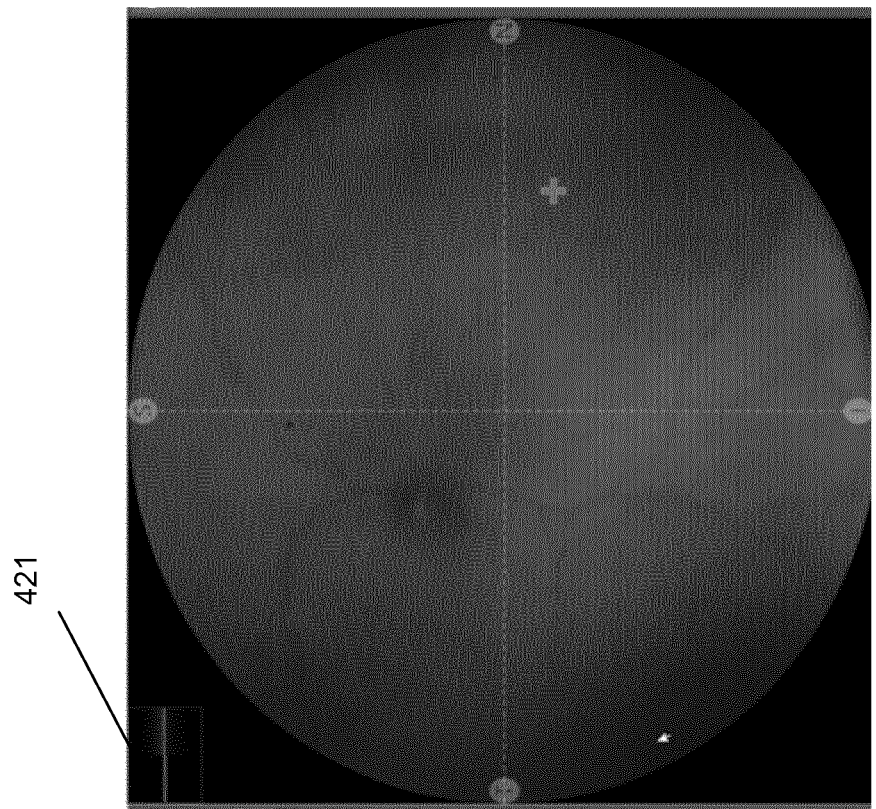
FIG. 4c
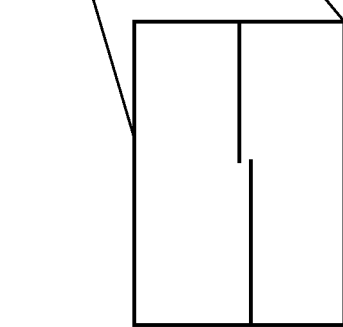
421
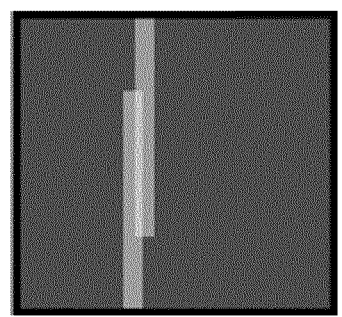
FIG. 4d

SYSTEMS AND METHODS FOR CHARACTERIZING REFRACTION WITH OPHTHALMIC IMAGING SYSTEMS

CROSS-REFERENCE TO RELATED APPLICATIONS

The present application is a National Phase application under 35 U.S.C. § 371 of International Application No. PCT/EP2018/058138, filed Mar. 29, 2018, which claims priority to U.S. Provisional Application Ser. No. 62/543,709, filed Aug. 10, 2017, and U.S. Provisional Application Ser. No. 62/479,786, filed Mar. 31, 2017, the contents of each of which are hereby incorporated by reference in their entirety.

BACKGROUND

The need for focus aids and autofocus in camera systems is a common problem. This problem has generally been solved by measuring the impact of defocus on the imaging system, sometimes with additional features added to the imaging path to make the effects of defocus more visible. A simple example of an imaging based focus aid is the "ground glass" focusing screen in the viewfinder of a single lens reflex (SLR) camera. The screen is placed at the imaging plane of the camera, and one judges the focus of the camera by the sharpness of the image on it. Another example in an SLR camera is the split image focusing aid in the viewfinder. This involves a circle in the center of the focusing screen, divided into two portions by a horizontal, vertical, or diagonal line. The central part of the scene is seen through this circle, without substantial blurring even if the focus is slightly incorrect. However, if the focus is incorrect, even by a small amount, the two halves of the image in the circle will not precisely line up. The human eye is very sensitive to such misalignment, and thus the photographer can readily bring the focus to the proper point. FIG. 1 shows a diagram of how these two focusing aids work. FIG. 1a illustrates a top view, with the object plane imaged to ground glass and prisms. FIG. 1b illustrates the side view, with the object plane imaged in front of focus aids. Adjusting the focus of the camera to bring the image plane to the ground glass and prism pair would makes the image sharp on the ground glass and eliminate the displacement between the views through the prism pair.

Autofocus systems often follow a similar approach, imaging the same portion of the object from different collection angles, and then using cross-correlation to determine the shift between the images, and therefore the defocus. Another approach to focus aids is to split line projection (see for example US Patent Publication No. 2007/0253688 hereby incorporated by reference) which is similar to the projection prism pair focus aid in the SLR, but instead of collecting light through the prisms, marks are projected onto the object through the prisms, and then visualized through the imaging system. A relative displacement between these marks then indicates defocus.

In an emmetropic (normal) eye, the eye length and refractive power of the eye lens are matched, allowing images to come in to proper focus on the retina. Ametropia is a condition of the eye in which images fail to come to a proper focus on the retina due to a discrepancy between the eye length and refractive power of the eye lens. This discrepancy is generally described as the refractive error, or refraction, of the eye. Eye refraction is usually measured in the central vision, meaning the focusing of light on the fovea. Variations in the shape of the eye and the field curvature of the ocular media cause the eye's refraction to vary as one moves away from the central vision. This refraction as a function of position across the retina, or field of view, is known as peripheral refraction, and the difference between the refraction at the center of the retina (fovea) versus points in the periphery is known as relative peripheral refraction. When imaging an eye with an ophthalmic imaging system, it is necessary to match the focal setting of the imaging system with the refraction of the eye to generate an in focus image.

SUMMARY OF THE INVENTION

Here we describe a new approach for characterizing refraction with an ophthalmic imaging system. In some embodiments, this can be accomplished by taking advantage of the unique illumination system of a slit scanning ophthalmoscope, and enables measurement of eye refraction over the entire field of view of the imaging system. This eye refraction measurement can be used both for setting of instrument focus to minimize defocus and obtain the clearest image of the particular eye being imaged and to provide clinically meaningful information about the condition of the eye being examined.

In one embodiment, refraction is characterized using an ophthalmic imaging system. The method comprises illuminating a region of the retina along a first illumination path passing through a first location on the pupil of an eye using a light source, collecting light returning from the region of the retina on a detector, wherein the returning light travels along a collection path and passes through a second location on the pupil distinct from the first location, determining a shift in the location of the collected light on the detector relative to a predetermined location on the detector, said shift corresponding to the mismatch between the refractions of the ophthalmic imaging system and the eye, and storing or displaying the determined shift or a further analysis thereof. In some embodiments, the ophthalmic imaging system is a slit-scanning ophthalmoscope. The determined shift can be used to focus the ophthalmoscope and/or to assess the condition of the retina. In some embodiments, the light source is directed to illuminate multiple regions on the retina and the collecting, determining, storing or displaying steps are repeated for each illuminated region. In some embodiments, a second light source is used to illuminate a second region on the retina and the difference in shifts is determined. In some embodiments, the pattern of light illuminating the retina is rotated and the determined shifts are used to calculate one of spherical focus, astigmatism and orientations of astigmatism, or other optical aberrations.

In another embodiment, refraction is characterized using an ophthalmic imaging system by illuminating a first region of the retina of an eye with a first light source along a first illumination path, said first illumination path passing through a first location on the pupil of the eye, collecting light returning from the first region of the retina on a detector, illuminating a second region of the retina with a second light source along a second illumination path, said second illumination path passing through a second location on the pupil of the eye different from the first location on the pupil, collecting light returning from the second region of the retina on the detector, determining the difference in the shifts in the locations of the collected light for the two illumination paths, and storing or displaying the difference in the shifts or a further analysis thereof. This method is particularly desirable for an eye that has been dilated as it requires a larger pupil for the separate beam paths. To optimize the accuracy of the measurements, the first and second regions of the retina may be nearly the same for the case where the refraction offset is nearly zero, and the two illuminations may be done sequentially so as to measure the two shifts without interference between them. The imaging system can be a slit-scanning ophthalmoscope. The determined shifts can be used to focus the slit-scanning ophthalmoscope or to evaluate the refractive condition of the retina. An alignment aid can be provided to aid in patient fixation. In some embodiments, the light source is directed to illuminate multiple regions on the retina and the collecting, determining, storing or displaying steps are repeated for each illuminated region. In some embodiments, the pattern of light illuminating the retina is rotated and the determined shifts are used to calculate one of spherical focus, astigmatism, orientations of astigmatism, or other optical aberrations.

The features and advantages described herein are not all-inclusive and many additional features and advantages may be apparent to one of ordinary skill in the art in view of the figures and description. Moreover, it should be noted that the language used in the specification has been principally selected for readability and instructional purposes and not to limit the scope of the inventive subject matter.

BRIEF DESCRIPTION OF THE DRAWINGS

FIG. 1a shows the top view of a prior art auto-focusing system in an SLR camera employing ground glass and a pair of prisms.

FIG. 1b shows the side view of the prior art SLR auto-focusing system depicted in FIG. 1a.

FIG. 2b is a simplified illustration of an eye being imaged with a slit scanning ophthalmoscope.

FIG. 2c is a simplified illustration of a slit scanning ophthalmoscope having two distinct illumination pathways imaging an emmetropic eye.

FIG. 2d is a simplified illustration of a myopic eye being imaged with a slit scanning ophthalmoscope with two illumination pathways.

FIG. 2e is a simplified illustration of a hyperopic eye being imaged with a slit scanning ophthalmoscope with two illumination pathways.

FIG. 4c illustrates how the level of defocus can be displayed along with an image of the retina.

FIG. 4d illustrated an alternative approach for displaying the defocus characterization.

DETAILED DESCRIPTION

The following definitions may be useful in understanding the detailed description:

Eye refraction: Discrepancy between eye length and refractive power of the optics in the eye, leading to objects at infinity appearing out of focus on the retina. Measured in diopters.

Foveal eye refraction: Eye refraction for the central vision, or fovea. The foveal eye refraction is what is typically measured at an optometrist's office.

Peripheral eye refraction: Eye refraction as a function of position across the field of view, or position on the retina, particularly in the peripheral part of the eye. Also shortened to peripheral refraction.

Relative peripheral refraction: Difference between the refraction at the center of the retina (fovea) versus other points on the retina Ophthalmic system refraction: Refractive power of an ophthalmic system across the field of view, measured in diopters. An ophthalmic system that focuses at infinity would have a refraction of 0 diopters. We use the term ophthalmic system herein to refer to a system for characterizing the eye, not the eye itself.

Defocus: Mismatch between eye refraction and ophthalmic system refraction at a specific point on the retina, typically the fovea.

Refraction offset: Mismatch between eye refraction and ophthalmic system refraction across the field of view of the ophthalmic system.

Field curvature: Variation in refraction across the field of view.

All patent and non-patent references cited within this specification are herein incorporated by reference in their entirety to the same extent as if the disclosure of each individual patent and non-patent reference was specifically and individually indicated to be incorporated by reference in its entirety.

Figure 2A:
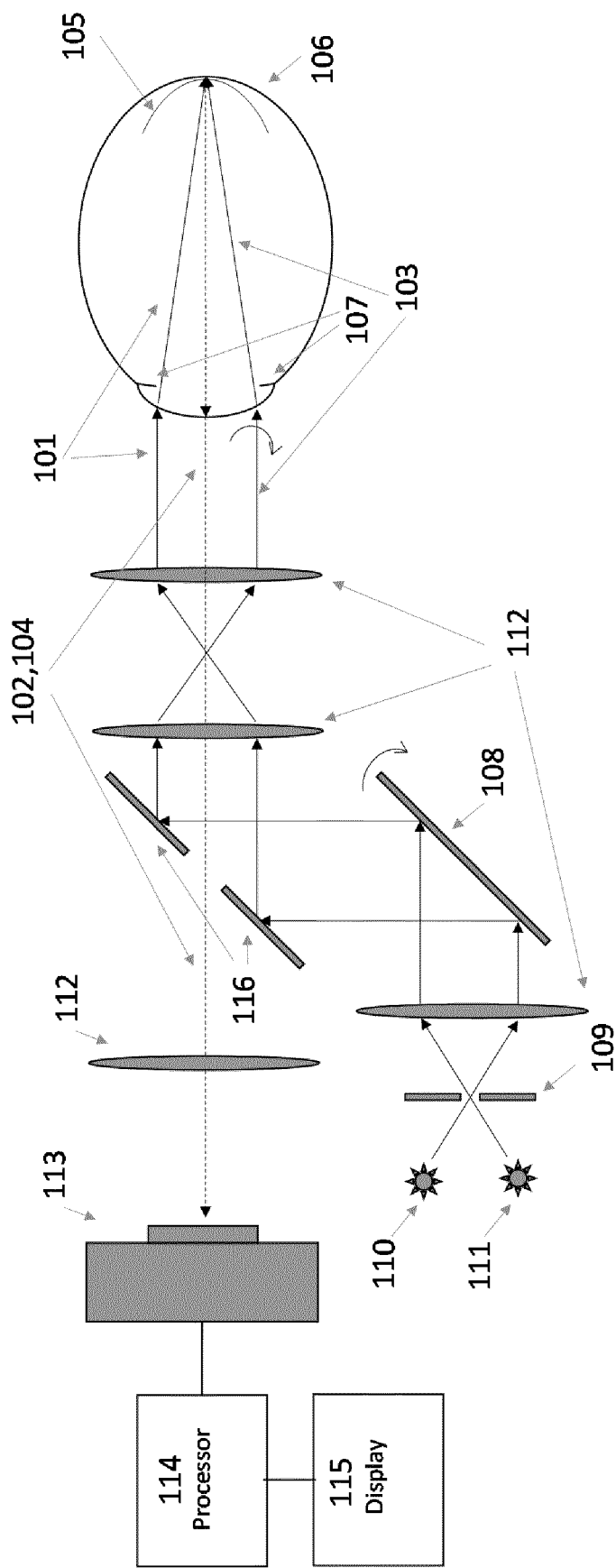
FIG. 2a is a schematic illustration of one embodiment of a slit scanning ophthalmoscope capable of carrying out the refraction characterization of the present application.

FIG. 2a illustrates one embodiment of an ophthalmic imaging system capable of characterizing refraction according to various embodiments of the present application, in this case it is a slit-scanning ophthalmoscope. Illumination light from sources 110 and 111 travels through a horizontal illumination slit 109 and a lens 112, creating upper and lower illumination beams, 101 and 103. These illumination beams are scanned across the retina by a rotating mirror 108, which is imaged to the eye pupil 107, causing the beams to pivot vertically at the eye pupil 107. The horizontal slit 109 is imaged by the optics to the retina, creating a horizontal line of illumination 105 on the retina at the back of the eye 106. The rotation of mirror 108 causes this illumination line 105 to sweep vertically across the retina. Light returning from the retina after illumination from the upper and lower illuminations follow paths 102 and 104 respectively, passing through the splitting mirror 116 to the detector, likely a camera 113, which is imaged to the retina at the back of the eye. By illuminating the two paths and collecting the returning light from the illuminations sequentially, it is possible to measure the effect of the optical system on these two illumination paths independently. The signal from the light collected by the camera 113 as the beams are swept across the retina is processed by processor 114. The results of the processing can be stored in the processor 114 or other storage medium or be displayed as an image or a further analysis thereof on display 115. This unit could be dedicated to data processing or perform other tasks which are quite general and not dedicated to the imaging device. The processor 114 may contain for example a field-programmable gate array (FPGA), a digital signal processor (DSP), an application specific integrated circuit (ASIC), a graphics processing unit (GPU), a system on chip (SoC) or a combination thereof, that performs some, or the entire data processing steps, prior to passing on to the host processor or in a parallelized fashion.

If the illumination slit 109 is properly imaged to the retina, the upper and lower illumination beams hit the retina in the same region, and paths 102 and 104 are superimposed as shown in the diagram. If illumination slit 109 is not well focused to the retina, illumination paths 101 and 103 will be displaced vertically relative to one another on the retina, and paths 102, and 104 will be slightly displaced, causing a relative displacement or shift on the camera of the illumination regions from the two illumination beams. By illuminating along the two beam paths sequentially, we are able to measure the displacement of each of the illuminations independently and therefore determine the relative displacement. One aspect of this invention is the use of this displacement to characterize the eye refraction across the field of view of the ophthalmic system. This can be accomplished by determining the refraction offset between the eye and the ophthalmic system based on this displacement, and then combining this with the ophthalmic system refraction to determine the eye refraction.

A simplified diagram of an eye being imaged by a slit scanning ophthalmoscope is shown in FIG. 2b. An illumination light beam follows path (1), entering the eye at one location on the pupil, and then returning along path (2), passing through a different location on the pupil. The light from illumination path (1) spreads out horizontally, illuminating a horizontal stripe (5) across the retina. This horizontal stripe is swept vertically across the retina (indicated by arrow 7) by rotating the input beam (arrow 8), and the returning light is collected on the camera, generating an image of the back of the eye. The reason for the separation between illumination path and collection path is to stop reflections from the cornea and imaging optics from creating artifacts on the image (see for example, U.S. Pat. No. 9,456,746, hereby incorporated by reference). Apertures are typically placed in the system to block stray light, where one aperture would be conjugate to the cornea, limiting the collected light to the region of the cornea that path (2) passes through, and another aperture would be conjugate to the retina, limiting the collected light to that light which appears to come from the illuminated region of the retina. As shown in FIG. 2c, where an additional illumination path (3) has been added, one could also have multiple illumination paths and/or multiple collection paths. FIG. 2c shows the case of an emmetropic eye (6) (meaning that eye is focused at a distance approximating infinity) where the illumination is set to match (upper and lower illuminations are both parallel to the optical axis, such that they meet on the retina at the center of the retina). As the camera is imaged to and aligned to the retina, the light returning from the retina from both beams returns to the center of the sensor. Sweeping the beams, as shown in FIG. 2b, will cause both illuminations to sweep across the camera together, assuming that the eye has no relative peripheral eye refraction and that the ophthalmoscope exhibits minimal field curvature.

In the configuration shown in FIGS. 2b and 2c, the light sweeps across the camera as it is swept across the retina. This is sometimes referred to as an imaged or non-descanned configuration. PCT Publication WO 2012/059236 and US Patent Publication No. 2015/0131050, hereby incorporated by reference, describe several embodiments of slit scanning ophthalmoscopes including other designs where the light is swept across the camera as shown above, and also descanned imaging schemes where the optical system is such that the light returning from the eye that is collected for different illumination strips is detected on the same region of the camera and the image is built up in a processor. Like the system of FIG. 2a, the system of FIG. 2b could be operably connected to a processor (not shown) for receiving the images from the camera and performing further analysis thereto. A display may be operably connected for displaying images or the results of the further analysis to the instrument operator as well as for providing a user interface to the operator for guiding the image acquisition.

As the illumination system for the imaging configuration in FIG. 2c is two horizontal strips of light that enter the pupil at positions that are vertically displaced from the collection aperture, changes in the eye refraction will shift the illuminations vertically relative to the collection. This is shown for a long, myopic eye in FIG. 2d, where the light returning from the upper illumination (1) is shifted upward on the camera (2) from the expected central position illustrated in FIG. 2c for an emmetropic eye and the lower illumination (3) is shifted downward when it reaches the camera (4). FIG. 2e illustrates the case for a shorter, hyperopic eye, where the beams are shifted in the opposite directions, where the upper illumination (1) is shifted downward on the camera (2) and the lower illumination (3) is shifted upward (4). By measuring this shift in illumination on the camera relative to the position for an emmetropic eye, either measuring the shift of an individual beam, or the relative shift between the two sequential illuminations, we can determine the eye refraction after correcting for the ophthalmic system refraction. This shift is proportional to first order to the refraction offset between the ophthalmic system and eye, although the amount of shift per diopter of refraction may be dependent on the field position/location on the detector/camera. Note that rotating or shifting the eye can cause the retinal image to move on the camera, but this will have little effect on the displacement of the returning illumination on the camera.

Now consider how this effect can be used both for measuring the refraction across the field of view of a human eye and for setting the focus of a slit illumination ophthalmoscope. First, illuminate a region of the retina at any given location with a slit illumination with the orientation of the long axis of the slit illumination substantially in the direction orthogonal to the axis between the illumination and collection pupil. For simplicity, we will assume that the illumination slit is horizontal and the illumination and collection pupils are shifted vertically (perpendicular to the long axis of the slit) as is shown in FIG. 2c, but any orientation of the slit could be used. Next, collect light returning from the eye on the camera sensor over a region sufficiently tall to capture any vertical shifts in the illumination. As described earlier, there is a known or predetermined position on the sensor corresponding to illumination at best focus at the retina. Any shift in the illumination relative to this known position in the vertical direction, along the axis between the illumination pupil and detection pupil, will indicate a difference in the refractions between the ophthalmic imaging system and the eye.

Figures 5A, 5B:
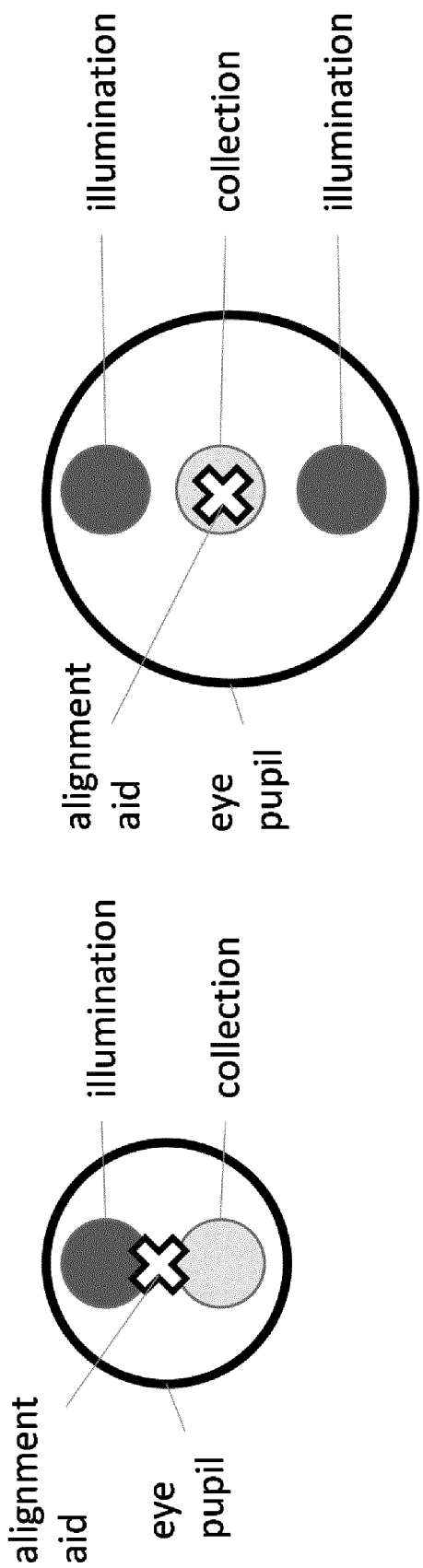
FIG. 5a illustrates the illumination, collection and alignment aid locations on the pupil of the eye for non-mydriatic imaging.
FIG. 5b illustrates the illumination, collection and alignment aid locations on the pupil of the eye for mydriatic imaging.

Note that adding a second illumination through the pupil on the opposite side of the collection aperture leads to a requirement for a larger pupil assuming that one keeps the initial illumination and collection apertures the same (see FIGS. 5a-b.) The pupil can be dilated by adding mydriatic drops, but this is not always desirable as it has a short term impact on the person's vision. Imaging through pupils that have not been dilated with mydriatic drops is generally referred to as non-mydriatic or non-myd imaging, versus myd or mydriatic imaging in the case when the drops are used. As the pupil size varies between humans, the initial pupil size prior to dilation may not be sufficient for adding the second illumination. Therefore it is desirable for the ophthalmic imaging system to have two modes, one using a single illumination area on the pupil and the other using an additional illumination area for mydriatic imaging. In the case where there is a single illumination area offset relative to the collection area, (i.e. with the second illumination area turned off) the optimum pupil alignment to minimize the required pupil size would be when the center of the pupil is aligned to a point between the illumination and collection, shown as an x in FIG. 5a. In the case where there are illumination areas on opposite sides of the collection area, the optimum alignment is when the center of the collection aperture is centered on the pupil, as shown in FIG. 5b. Given the changes in the alignment requirements depending on whether one is doing non-myd or mydriatic imaging, it is desirable to have alignment cues that are adjusted between myd and non-myd imaging along with the change in illumination. In particular, the alignment center could shift from the center of the collection region in the mydriatic image case with symmetric illumination to having the alignment center be between the illumination and collection region in the non-myd case where there is no illumination on the other side of the collection.

Figure 3:
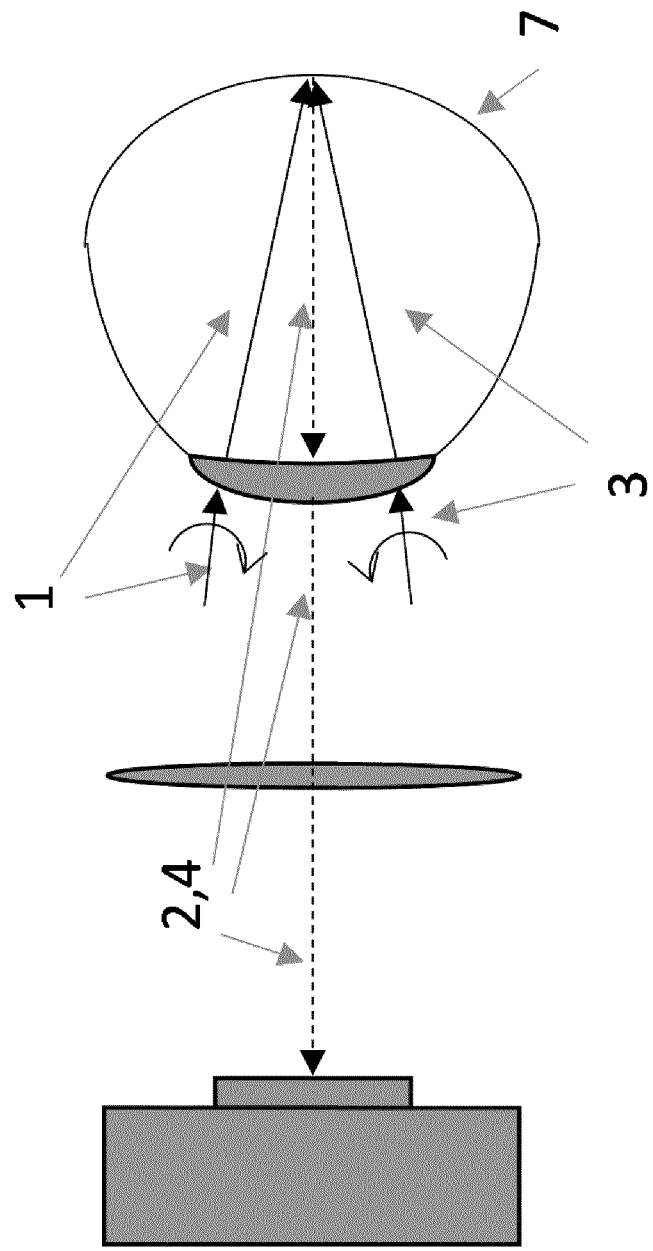
FIG. 3 is a simplified illustration of a slit scanning ophthalmoscope with focus optimized for a hyperopic eye.

In the description of FIG. 2 above, the illumination system was set for an emmetropic eye (illumination entering the eye parallel to the optical axis of the eye.) As shown in FIG. 3, the shift in the position of the illumination beams on the camera seen in the hyperopic eye of FIG. 2e can also be eliminated by matching the vergence of the illumination beams to the refraction of the eye, or said differently, for an imaging system where the illumination and collection optics are focused together, by bringing the camera into focus. Thus, the slit scanning ophthalmoscope can be focused onto the retina by adjusting the focus of the optics so as to bring the illumination strip to a predetermined location on the camera, or in the case of multiple illumination paths, so as to bring the illuminations to a predefined position relative to one another on the camera, preferably being superimposed. As these shifts can be measured by a computer, this can be done in automated fashion, leading to autofocus. The locations of the illuminations on the camera would typically be based on the vertical centroid of the illumination near the center of the retina so as to bring the center of the retina into best focus. As the refraction of the eye tends to shift relatively monotonically as one goes from the center of the eye to the periphery, one might want to autofocus the camera to a point in the retina that is slightly off-center to reduce the level of defocus at the periphery of the image.

Using this principle, a closed loop system can be developed to automatically focus the ophthalmic imaging system on a region of interest on the retina. This autofocus system can be designed to operate in both mydriatic and non-mydriatic imaging modes, with the only difference being the required input data. In mydriatic mode, the required input data would be the locations (most likely the centroids) of the returning light on the camera from the multiple (preferably two) sequential illumination paths going into the eye. In non-mydriatic mode, it would be the location (most likely the centroid) of the returning light on the camera for the single beam going into the eye. As the two illuminations in mydriatic mode share the same optical path, any variations in alignment (error in galvo position or shift in a mirror) should affect the position of both illuminations equally, and thus one can cancel these effects by measuring the relative position on the camera of the light from the two illumination paths. In the case of non-mydriatic imaging, where there is a single illumination path, it may be desirable to have an internal target in the system, where the light incident upon and returning from this internal target onto the camera can be used as a reference to measure and remove any effects of misalignment in the system. Although not as critical, this target could also be used to measure any misalignment in the multi-illumination path (mydriatic mode).

Although the ophthalmic imaging system has been described relatively simplistically here, one should recognize that the aberrations in the optical system of the fundus imager may lead to a variation across the field of view both in the amount of shift for a given eye refraction, and per diopter as the camera focus is adjusted. Considering these effects, while still assuming a linear behavior of the system, the shift in the measured illumination on the detector can be written as:

$Rom(x,y)=p_0(x,y)+Rx(x,y)*r(x,y)+P*p(x,y)$, where:
1) $Rom(x,y)$=measured shift in illumination
2) $x,y$=position in field
3) $p_0(x,y)$=field dependent shift caused by camera's optical aberrations
4) $Rx(x,y)$=patient's field dependent eye refraction in diopters
5) $r(x,y)$=field dependent illumination shift per diopter of patient's eye refraction
6) $P$=camera focus setting in diopters
7) $p(x,y)$=camera's field dependent illumination shift per diopter of focal adjustment Additional effects, such as changes in camera magnification with focus could create a second order non-linear effect that one could compensate for with a more complex equation. Re-arranging this equation, one could then determine the patient's field dependent eye refraction based on the measured field dependent shift in illumination as: $Rx(x,y)= [Rom(x,y)-p0(x,y)-P*p(x,y)]/r(x,y)$, where $r(x,y)$, $p(x,y)$, and $p0(x,y)$ could be determined using various possible approaches, including theory, simulation, or experimental measurements. Note that in this equation, "$[-p0(x,y)-P*p(x,y)]/r(x,y)$" is the ophthalmic system refraction, and "$Rom(x,y)/r(x,y)$" is the refraction offset.

Figure 4A:
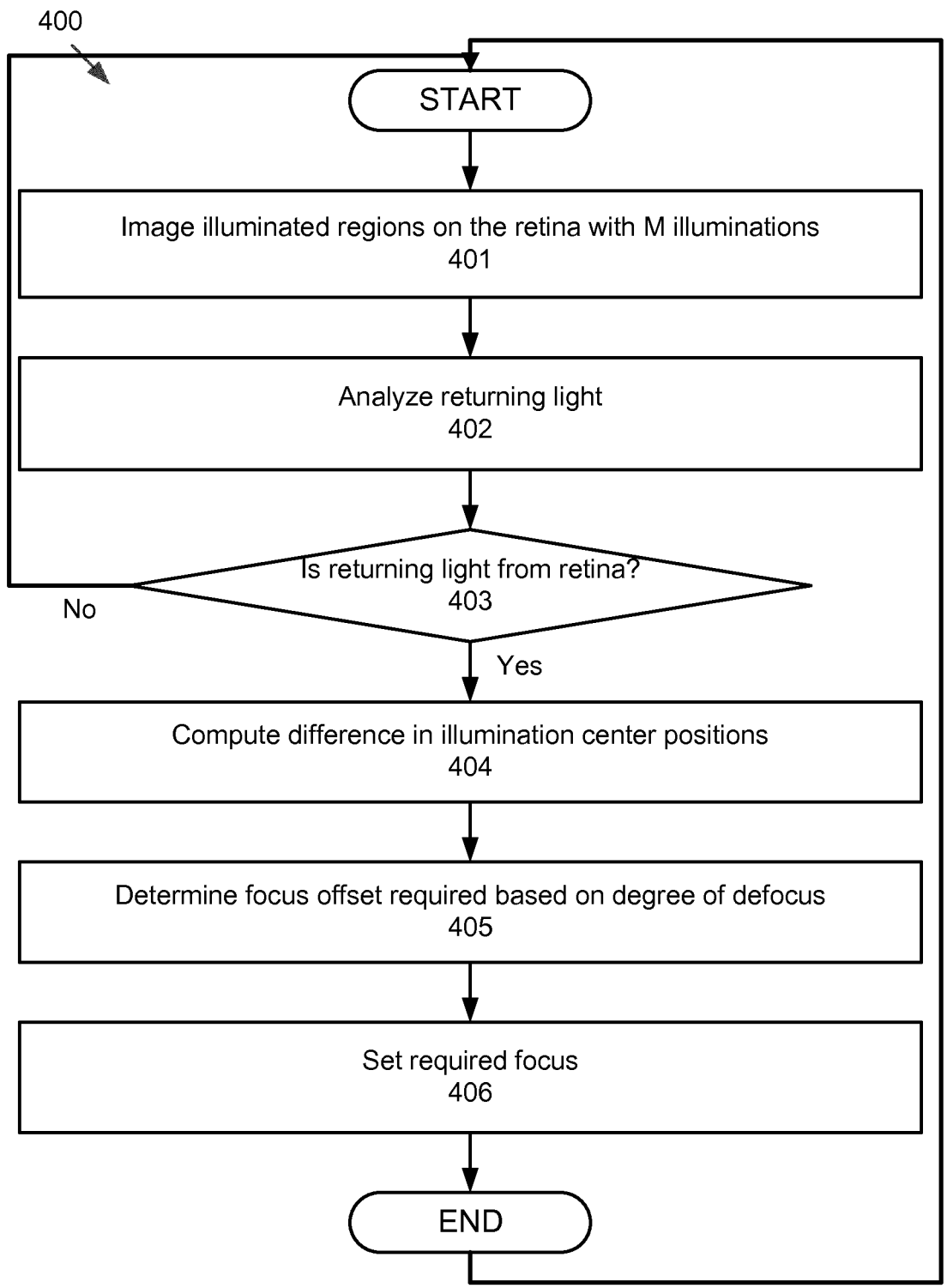
FIG. 4a is a flow chart of the steps involved with auto-focusing an ophthalmoscope for mydriatic imaging.

FIG. 4a illustrates the autofocus workflow for mydriatic mode. First the retina is illuminated with M sequential illuminations (401). Then the illuminations coming from the retina are analyzed to ensure they are from the retina and not from an eyelid during a blink (402). If they are confirmed to be light returning from the retina (403), the difference in the center location of the two beams is computed (404) and a measure of relative defocus is calculated (405). By relative defocus we mean the difference between the ideal focus for this retina and the focus at the time when the image was acquired. With this information, a new required focus setting is established, by adding the relative defocus to the current focus setting (406). As shown in the diagram, once the newly calculated focus is set, one could return back to the beginning of the process and start again. There are a number of cases where one might want to do this including, but not limited to:

1) If the focus offset (defocus) is reasonably large, requiring a large correction, and there is some uncertainty on the correction, one may wish to cycle through the process a few times so as to iterate in to the optimum focus. As the correction becomes smaller, it is likely to be more accurate, thus allowing more precise focusing.
2) Prior to the onset of presbyopia, the eye has the ability to adjust its focus. Other effects like changing the distance from the instrument to the eye may also impact the focus. Therefore it may be desirable to continuously adjust the focus of the instrument to maintain optimum focus.
3) There may be some trigger which causes the process to restart. Examples of such triggers include, but are not limited to selection of acquisition by the operator, measured focus error being greater than some threshold, and change in the fixation position causing the instrument to focus on a different part of the retina.

Figure 4B:
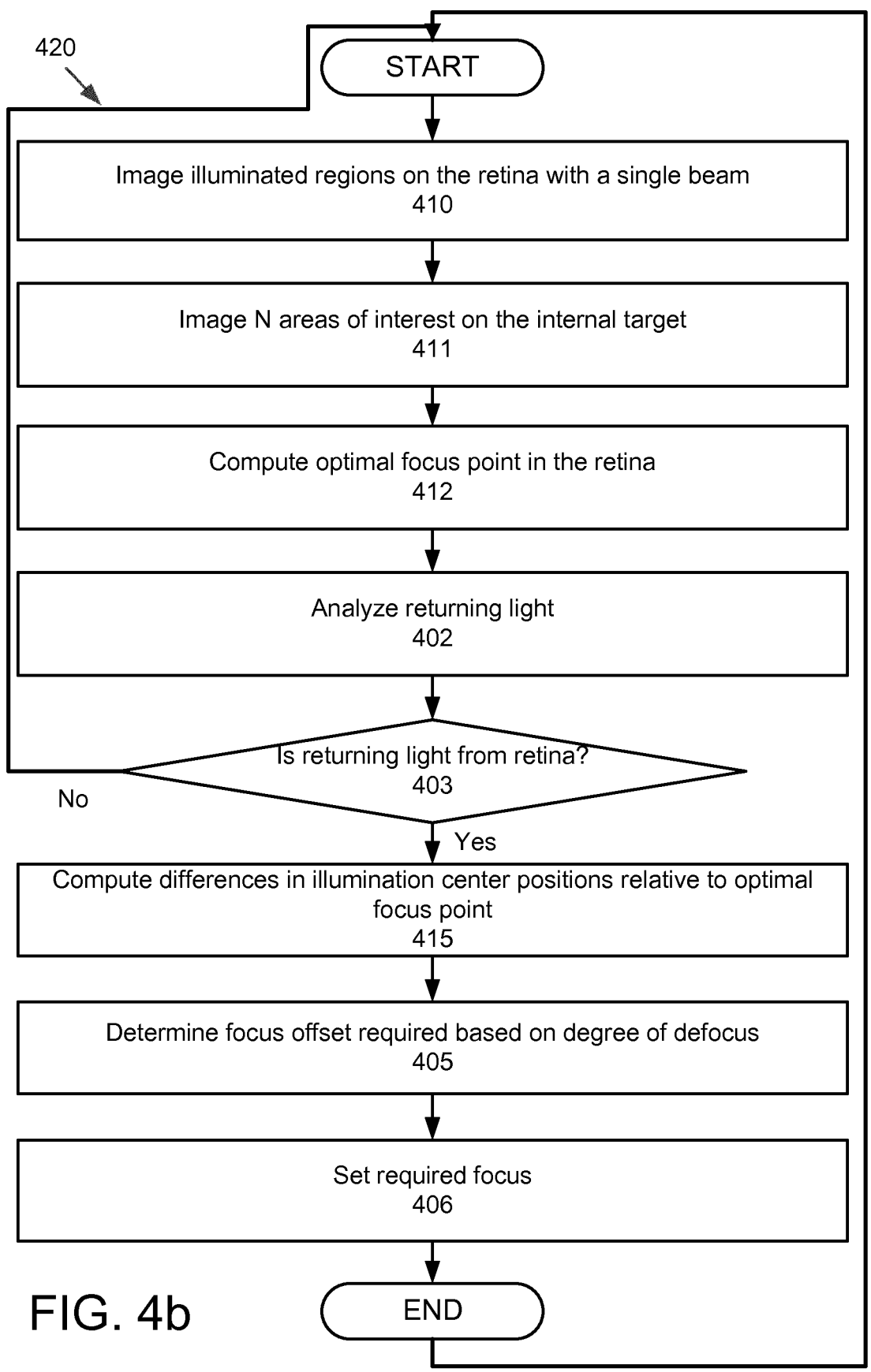
FIG. 4b is a flow chart of the steps involved with auto-focusing an ophthalmoscope for non-mydriatic imaging.

FIG. 4b illustrates the autofocus workflow in non-mydriatic mode. In this mode, there is only one Illumination entering the eye (410). One can determine the amount of defocus by measuring the displacement of this illumination on the camera relative to where it would have been in a perfectly focused system. However, without the second illumination position on the pupil available in the mydriatic mode to cancel alignment errors, this measurement is susceptible to alignment drift. To address this potential alignment drift, an internal target can be installed, preferably at a location such that the illumination slit and camera can be imaged to it with any parts of the optical system that are susceptible to alignment drift (moving optics) between this target location and the illumination slit.

By illuminating this target at one or more locations N (411) and measuring the illumination position of the light returning from this target onto the camera, one could determine any drift in alignment of the optics between the illumination slit and this target, and therefore remove these effects from the measured displacement of the illumination light returning from the eye onto the camera. The potential multiple locations could be multiple positions along the line illumination, and/or different illumination regions addressed by rotation of the rotating mirror. Once any displacement due to alignment drift has been removed, the remaining shift in the illumination position can be used to determine where the optimal focus point in the retina should be (412). The process of auto focus then becomes the same as with the mydriatic mode including analyzing the images (402), assessing whether they are valid retina images (403), determine focus offset (405) and set required focus (406), with the difference being that instead of calculating the defocus based on the two illumination beams returning from the eye, the displacement of the single illumination beam is used, potentially with additional information from the single illumination beam hitting the internal target (415).

In both imaging modes, the area that is focused can be changed by moving the illuminations on the retina to that location and then imaging those locations. The process of autofocus remains unchanged.

To aid the operator in determining whether the required area of interest is in focus, an indication of the level of defocus can be displayed on the user interface. In one embodiment as illustrated in FIG. 4c, the calculated level of defocus can be displayed (421) along with the current image as two horizontal lines with a vertical displacement proportional to the amount of defocus (meaning that they have no noticeable vertical displacement when the retina is in focus.) These two lines could either be slightly separated, touching tip to tip, or overlapping in the horizontal direction. One embodiment of an alternative display is illustrated in FIG. 4d where the two lines are displayed as semitransparent overlapping bars. As the focus condition changes, the vertical locations of the bars will be adjusted. The bright overlapping region provides an indication of the degree of defocus. When the area of interest is in focus, the bars will be horizontally aligned and there will be a central bright region with no semitransparent sections. In another embodiment, the illuminations on the region of interest on the retina can be shown along with an overlay showing the center positions of these illuminations. In non-mydriatic mode, the single illuminated region of the retina can be shown alongside with its center line as well as another image of equal size displaying a line of equal size of the center line above, which indicates the optimal focus position calculated using the internal targets. If the focus is incorrect, the two lines of the images will not line up. In mydriatic mode, it can show the N illuminations going into the retina, with their respective center lines and the operator can assess the focus or defocus of the region by comparing the difference in centers of these illuminated regions. As mentioned earlier, the human eye is very sensitive to such misalignment, and thus the photographer can easily determine whether the given region is in focus or not.

When imaging in mydriatic mode, it can be difficult for the operator to determine if both illuminations are entering the pupil, as the retina could be illuminated with just a single illumination which would produce an image on screen, but this image would be just from one illumination. To overcome this problem, the information used to autofocus can be further analyzed to determine if both illuminations are entering the pupil and give feedback to the operator on whether they need to move the instrument up or down. In order to determine this, the two beams that are used in auto focus are analyzed separately to determine if the images produced from these beams are valid retinal images. If one of them is and the other is not then this tells the operator that only one illumination is entering the pupil and therefore the instrument needs to be either raised or lowered respective to the patient's pupil. This information can either be relayed to the user graphically or, in the case of a robotically controlled system, can be used to move the instrument to the required height.

This concept for characterizing refraction can be generalized to the entire retina. If the slit of illumination is directed to multiple positions across the retina, the refraction offset over the entire field may be characterized. As mentioned above, shifts that are constant across the field are traditional focus errors which in some systems may be directly corrected by an adjustment to a refractive compensation device. On subsequent measurements, the error may be further compensated—thus a closed loop correction may be achieved. Variations in the refraction offset over the field of view of the retina are not corrected by simple focus correction, however they may still be useful for providing a best compromise over the full field. For simplicity, one could also measure the defocus at a single location (likely to be the center of the FOV, or location designed to minimize absolute deviation over a defined usable field) and use this to correct for the defocus in the system. For better accuracy in measurements of the peripheral eye refraction, one would likely first focus/autofocus the imaging system to remove the patient's foveal eye refraction, then measure the remaining refraction offset across the field of view of the fundus camera. Adding the refraction of the ophthalmic system would then provide the patient's peripheral eye refraction across the field of view of the camera.

Drift or errors in the alignment of the imaging system can also cause displacements of the illumination relative to the expected collection location of the camera. This effect can be compensated for (and to first order eliminated) with the second illumination beam shown in FIG. 2c. In this case, one would typically make two measurements, with one illumination on, and then the other, and measure the displacement for each case. Alignment errors or drifts will, to first order, cause both illumination positions on the camera to shift equally in the same direction, while defocus will cause them to shift independently, based on where they entered the pupil. Thus, the defocus will be proportional to the difference in shifts between the upper and lower illuminations, cancelling misalignment affects. If the refraction is being measured off-axis (in the periphery of the image), measuring the difference in displacement between two illuminations should also be helpful in cancelling shifts due to field distortions in the imaging optics. This optical field distortion can be measured for any given system or design (or determined through optical simulation.) Once the optical distortion is known, the relative position of the illumination and collection apertures can be optimized as a function of field position to minimize the required height of the active collection region on the camera for any given illumination. Minimizing the active region on the camera is desirable to minimize the acquisition time of the instrument. Note that if the optical distortion is known, one could also use just one illumination source, and then correct for the shift associated with optical distortion to determine the effect due to defocus (assuming that the instrument has been calibrated such that position of the illumination in the center of the retina at best focus is known). The two illumination source concept could be a general improvement and so can be used in slit scanning ophthalmoscope systems with and without defocus measurements.

It may be additionally useful to be able to calibrate the measurement using a test eye with known refraction characteristics as a system level test and certification. As described above, determination of defocus may be affected primarily by geometrical factors and the design of the camera. Using multiple acquisitions may also compensate small alignment errors and drifts. Additionally, a test eye measurement may be applied to the system at time of manufacture to finely characterize the system as built, but may also be applied at a testing site. Using a test eye calibration directly prior to imaging, may for example be used as input to account for short-term drifts in alignment, and may obviate the need for multiple measurements which may inconvenience the patient or be difficult due to non-mydriatic imaging.

Here we will use a real world example to provide detail on how a measurement of refraction of the eye can be made. Let us assume that we illuminate the retina during a sequence of infrared preview scans through one or two portions of the patient pupil that are displaced roughly ±1.5 mm from the center of the imaging path. If the pupil is dilated with mydriatic drops, or is otherwise sufficiently large, both illumination paths are used. For small pupils, only one illumination path, in this case the lower illumination, is used.

When the instrument is focused to correct the patient's foveal eye refraction, the illumination and imaging paths all meet at the retina. Given some defocus, $\Delta P$, between the instrument and the patient's eye, and the 1.5 millimeter displacement between the illumination and collection paths at the pupil, the two illuminations are misdirected by ±1.5 milliradians/diopter×$\Delta P$, relative to the angles that would cause them to meet at the retina. Thus defocus causes an easily-observable shift between the illumination stripes on the retina. For instance, assuming a fundus camera magnification of 100 pixels/°=6 pixels/milliradian, each diopter of defocus would shift the stripes by ±9 pixel-rows in the retinal image. Note that the variation in the magnification of the fundus image, among other effects, may cause this shift per milliradian to vary across the field of view, as described earlier. The amount of defocus, and therefore the shift in the stripes, will also vary across the retinal field as the refraction offset is a measure of the location of the surface of the retina relative to the focal plane of the optical system, where the optical system includes the optics of the fundus camera and of the eye, and both have field curvature. To map the peripheral refraction of the human eye alone, one would add the focal power of the fundus camera (ophthalmic system refraction) to the refraction offset measurement, both of which will likely vary across the field of view.

Assuming that one is using two illuminations, it is highly desirable to image the same region of the retina for the case where the image is in focus. One way to ensure this is to use a single horizontal slit aperture imaged to the retina, and place two illumination sources (e.g. LEDs or lasers) behind the aperture with a vertical displacement between them. As the light from the two sources passes through the same aperture, they will appear at the same position on the retina when the aperture is imaged to the retina, but will be displaced vertically as described earlier if the aperture is not imaged to the retina. As stated earlier, one would illuminate the two beams sequentially to more easily isolate the displacements of each one. Note that the same configuration could be set up with any arbitrary orientation (vertical slit, horizontal slit, or anything in between) as long as the illumination sources have a displacement relative to one another in the direction perpendicular to the slit. Note also that, although the preferred embodiment involves scanning a strip of light across the retina to measure multiple points on the retina simultaneously along the strip, one could also scan other alternate illumination areas (multiple parallel strips, single spot, or multiple spots for example) across the retina and measure the displacement of these illumination areas.

By sweeping the illumination across the retina and measuring the refraction while accounting for the ophthalmic system refraction, this method can map the peripheral eye refraction across the full field of view of the ophthalmic imaging system. As peripheral eye refraction is a probable factor in the development of myopia, this mapping of peripheral eye refraction may be a good technique for screening of candidates for myopia therapy, and may also be beneficial for designing spectacle lenses, contact lenses, or intraocular lenses that are customized for a person's eye either to improve peripheral vision by bringing the periphery more into focus, or to limit the development of myopia by adjusting the peripheral eye refraction so as not to trigger the myopia development. (It has been demonstrated in animals that making the eye hyperopic with a lens leads to the development of myopia, and correction of myopia in the central vision in humans typically leads to peripheral hyperopia.) Therefore, one way to protect against myopia development may be to prescribe a lens (as part of a pair of spectacles, or a contact lens) that makes the periphery of the eye (or parts of it) myopic, using this peripheral eye refraction measurement as an input to either design a lens, or select from a group of lenses.

We should also mention that this measurement of displacement measures the component of the refraction along the direction perpendicular to the slit only, and therefore astigmatism can lead to a refraction in the orthogonal direction. Many human eyes have astigmatism in the central vision. In addition, human eyes generally have increasing radial astigmatism and other aberrations as one moves from the center of the vision to the periphery. This radial astigmatism is likely to be radially symmetric to first order, but there may be additional variations in astigmatism both in individuals, and as part of the typical human anatomy. To generate a more complete picture of the eye, determining the spherical focus, astigmatism, and orientation of astigmatism, one could acquire multiple measurements with different orientations of the displacement between illumination and collection locations through the pupil. One example might be to collect three measurements with displacement between illumination and collection on the pupil at −45, 0, and 45 degrees relative to vertical. In an embodiment where the collection is through the center of the pupil, this would mean moving the illumination region to different points on the pupil, where the line between illumination and collection would be at −45, 0, and 45 degrees relative to vertical. As the displacement of the illumination on the retina due to defocus is in the direction of displacement between illumination and collection on the pupil, it would also be desirable to rotate the illumination line on the retina. One could also take only two measurements, which would give some information about astigmatism, or more than three measurements, which would give duplicate information and therefore confirmation of the measurements. Alternatively, one could combine the measurement of focus along one direction with either an assumption of rotational symmetry, and/or an eye model to derive an approximation of the peripheral eye refraction including astigmatism across the peripheral field.

Figure 8:
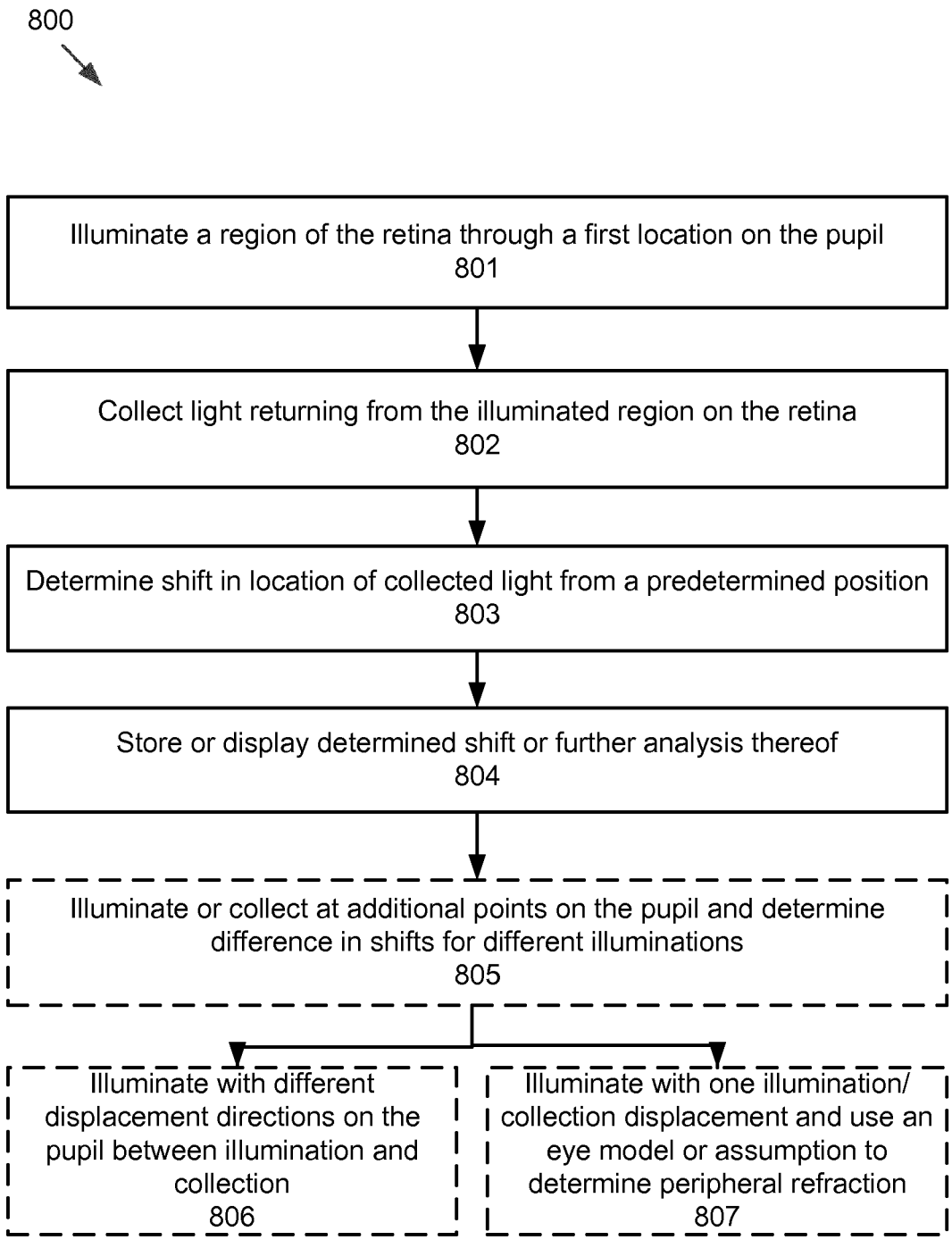
FIG. 8 is a flow chart of the basic steps involved with a refraction characterization according to some embodiments of the present application.

Although we have implemented this refraction measuring technique on a slit scanning ophthalmoscope, it can be generalized for any ophthalmic imaging system as follows and as illustrated in FIG. 8 with optional steps indicated in dashed boxes:

1) Illuminate a region of the retina, entering the eye at a given location on the pupil (801).
2) Collect the returning light from the illuminated region on a detector, the returning light traveling through a different point on the pupil than the illumination light (802).
3) Measure the displacement (shift) of the returning light on the detector relative to a predetermined location (803). In a preferred embodiment, the light is collected at a plane approximately imaged to the retina (measuring the displacement of the returning light at a plane further from the retinal image plane conjugate will also work, but probably will lead to a somewhat reduced measurement accuracy).
4) Store or display the determined shift (804). In some embodiments, a measure of refraction at the one or more regions on the retina is created based on this displacement of the light returning from the retina, in some cases. This measurement can be used to improve the focus of the ophthalmic system and/or characterize the refraction of the eye.
5) Optionally (indicated by dashes in figure), either illuminate or collect at multiple points on the pupil, and use the difference in displacements between the different pupil locations to provide a more robust measure of refraction (805).
6) Optionally (indicated by dashes in figure), make multiple measurements with different displacement directions on the pupil between illumination and collection to provide a more complete map of the refraction of the eye (806), with the particular potential benefit of measuring astigmatism and direction of astigmatism.
7) Optionally (indicated by dashes in figure), make a peripheral eye refraction measurement with illumination and collection displacement in one direction, and then use either an eye model, or an assumption of rotational symmetry of the human eye, to derive the approximate peripheral refraction in the direction orthogonal to the measurement (807).

Advantages of the approach described herein include the possibility of determining the eye refraction at multiple locations on the retina for a singular alignment of the overall optical system by just changing the location of the light on the retina. We use the term ophthalmic imaging system or imaging system to represent any system that directs light to the eye and collects light returning from the eye and whether it produces an actual image of the eye is not a requirement for the refraction characterization. In some embodiments, single points on the retina could be the regions to which the light is directed. The retina can be imaged to a camera to determine the displacements and therefore characterize the refraction without producing an image of the retina.

Figures 6A, 6B, 6C:
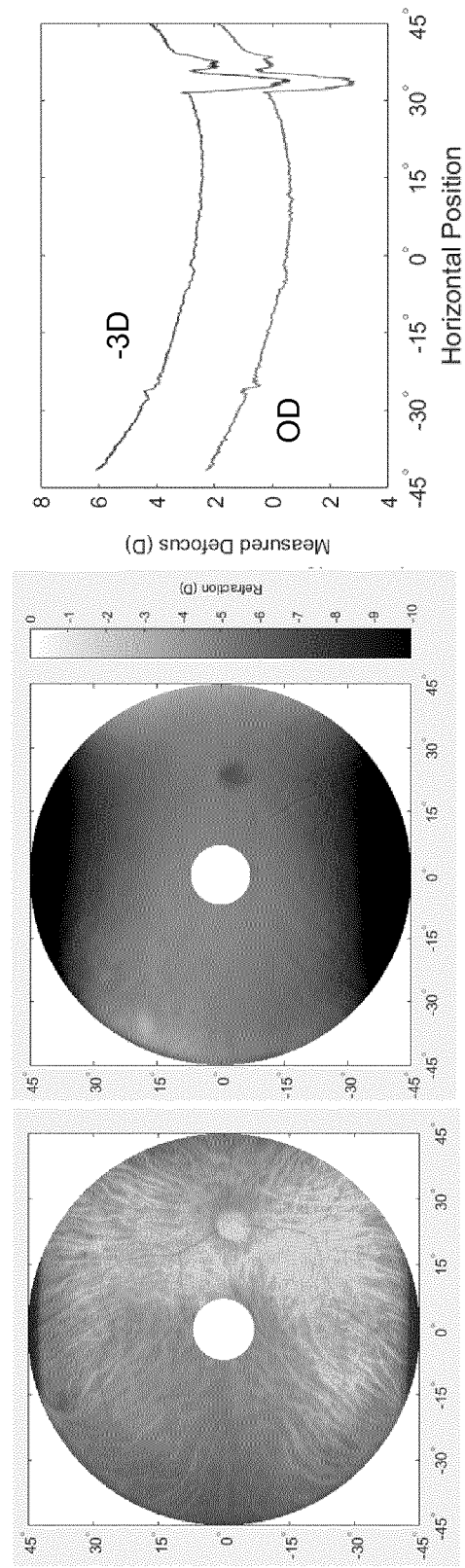
FIG. 6a illustrates a fundus image generated from a slit scan ophthalmoscope.
FIG. 6b illustrates a refraction map generated from a slit scan ophthalmoscope.
FIG. 6c shows the refraction measurements on a test eye for two different instrument settings where the focus is shifted by 3 diopters.

Mapping of peripheral eye refraction over a 90° FOV with a single acquisition using a widefield slit-scanning ophthalmoscope has been demonstrated. A wide-field fundus imaging system illuminated the retina with horizontal strips of light entering at the top and bottom of the pupil, providing the potential for measuring eye shape. By measuring the relative vertical shift on the retina between the upper and lower illuminations and accounting for any aberrations of the ophthalmic imaging system, a map of the vertical refraction of the eye across the full field of view of the imager can be created. The accuracy of the measurement was investigated using a test eye with different focal settings of the ophthalmoscope. As shown in FIGS. 6a-c, the system is capable of generating both a fundus image over the full 90° FOV (FIG. 6a), and a corresponding refraction map from the same data (FIG. 6b), providing precise registration for the eye refraction measurements. The saddle shape in the refraction map with lower values on the top and bottom of the map is a result of measuring only the vertical component of the rotational symmetric radial astigmatism in the eye. Additional images taken at plus and minus 45° rotation would be required to separate the overall eye refraction from astigmatism. The white circles in the middle of the images represent lens reflection areas, where reflections create artifacts in the images or prevent data from being collected. The accuracy of the measurement is demonstrated with a test eye in FIG. 6c. Two measurements are made with a 3 diopter shift in instrument focus, and the vertical refraction along a horizontal line is plotted for the two settings. As expected, a consistent shift of 3 diopters is seen between the plots. The dip in the curves in FIG. 6c is a result of a bump on the surface of a test eye.

Refraction offset is a measure of the offset of the focal plane of the retina relative to the focal plane of the optical system, where the optical system includes the optics of the eye. As the focal plane is a smoothly varying surface, the refraction will also be smoothly varying for a smooth retina. Any deformations in the surface of the retina will cause aberrations in the refraction map. Thus, in addition to measuring the overall refraction of the eye, one can obtain a measure of the topography of the retinal surface. This refraction characterization could therefore be used for detection of retinal shape abnormalities associated with disease, providing other information such as swelling caused by wet AMD, or retinal distortion associated with posterior staphyloma.

Figure 7:
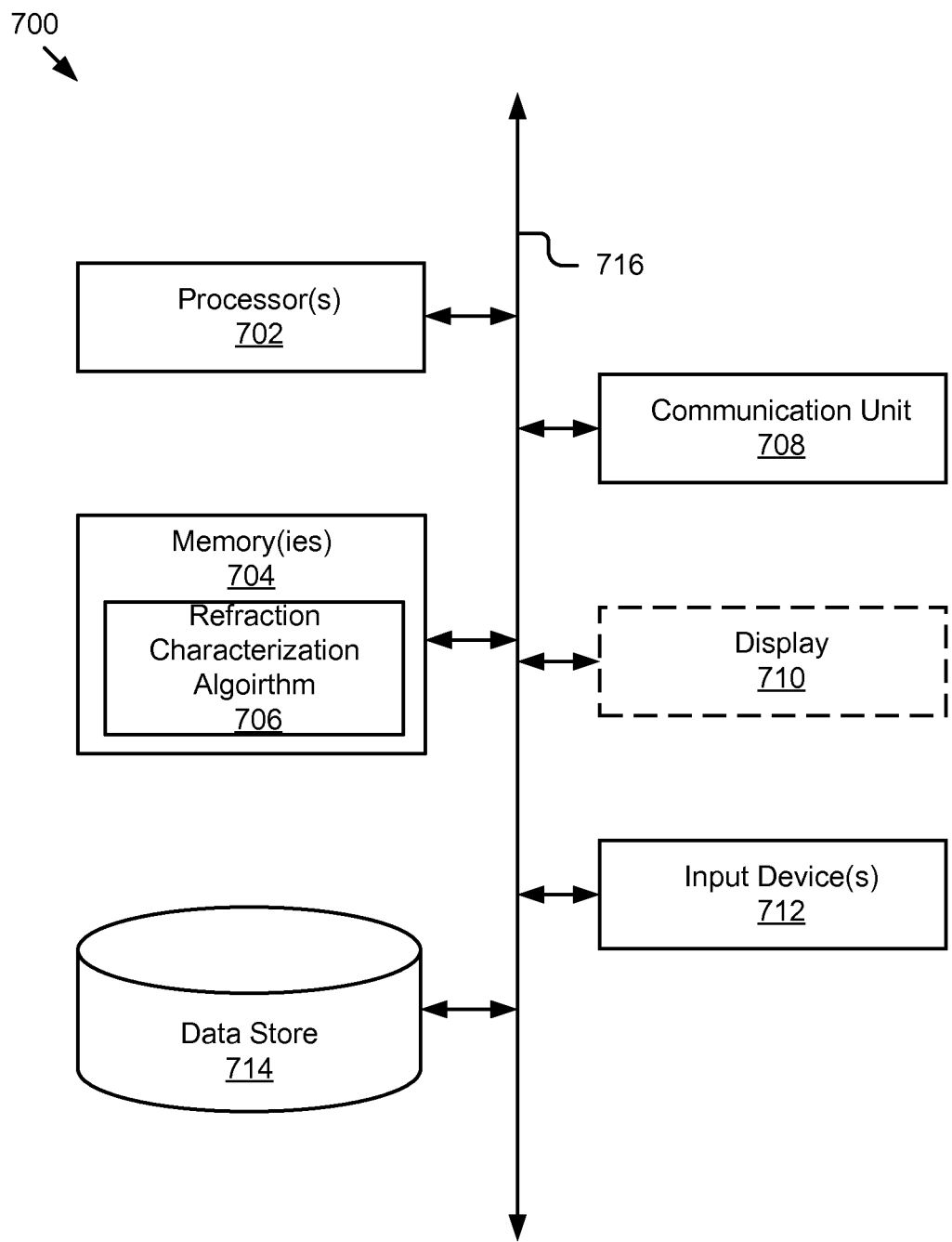
FIG. 7 is a block diagram of a general computer system that may perform functions discussed in this disclosure according to at least one aspect of the present invention.

The processing unit 114 that has been discussed herein in reference to FIG. 2a can be implemented with a computer system configured to perform the functions that have been described herein for this unit. For instance, the processing unit 114 can be implemented with the computer system 700, as shown in FIG. 7. The computer system 700 may include one or more processors 702, one or more memories 704, a communication unit 708, an optional display 710, one or more input devices 712, and a data store 714. The display 710 is shown with dotted lines to indicate it is an optional component, which, in some instances, may not be a part of the computer system 700. In some embodiments, the display 700 discussed herein is the display 115 that has been discussed herein in reference to FIG. 2a.

The components 702, 704, 708, 710, 712, and 714 are communicatively coupled via a communication or system bus 716. The bus 716 can include a conventional communication bus for transferring data between components of a computing device or between computing devices. It should be understood that the computing system 700 described herein is not limited to these components and may include various operating systems, sensors, video processing components, input/output ports, user interface devices (e.g., keyboards, pointing devices, displays, microphones, sound reproduction systems, and/or touch screens), additional processors, and other physical configurations.

The processor(s) 702 may execute various hardware and/or software logic, such as software instructions, by performing various input/output, logical, and/or mathematical operations. The processor(s) 702 may have various computing architectures to process data signals including, for example, a complex instruction set computer (CISC) architecture, a reduced instruction set computer (RISC) architecture, and/or architecture implementing a combination of instruction sets. The processor(s) 702 may be physical and/or virtual, and may include a single core or plurality of processing units and/or cores. In some embodiments, the processor(s) 702 may be capable of generating and providing electronic display signals to a display device, such as the display 710, supporting the display of images, capturing and transmitting images, performing complex tasks including various types of feature extraction and sampling, etc. In some embodiments, the processor(s) 702 may be coupled to the memory(ies) 704 via a data/communication bus to access data and instructions therefrom and store data therein. The bus 716 may couple the processor(s) 702 to the other components of the computer system 700, for example, the memory(ies) 704, the communication unit 708, or the data store 714.

The memory(ies) 704 may store instructions and/or data that may be executed by the processor(s) 702. In the depicted embodiment, the memory(ies) 704 stores at least a refraction characterization algorithm 706, which may include software, code, logic, or routines for performing any and/or all of the techniques described herein. For instance, the refraction characterization algorithm 706 may perform all or some of the operations depicted in FIGS. 4a and 4b for autofocusing the ophthalmoscope. In some embodiments, the refraction characterization algorithm could calculate the peripheral eye refraction. In some embodiments, the memory(ies) 704 may also be capable of storing other instructions and data including, for example, an operating system, hardware drivers, other software applications, databases, etc. The memory(ies) 704 are coupled to the bus 716 for communication with the processor(s) 702 and other components of the computer system 700. The memory(ies) 704 may include a non-transitory computer-usable (e.g., readable, writeable, etc.) medium, which can be any apparatus or device that can contain, store, communicate, propagate or transport instructions, data, computer programs, software, code, routines, etc. for processing by or in connection with the processor(s) 702. A non-transitory computer-usable storage medium may include any and/or all computer-usable storage media. In some embodiments, the memory(ies) 704 may include volatile memory, non-volatile memory, or both. For example, the memory(ies) 704 may include a dynamic random access memory (DRAM) device, a static random access memory (SRAM) device, flash memory, a hard disk drive, a floppy disk drive, a CD ROM device, a DVD ROM device, a DVD RAM device, a DVD RW device, a flash memory device, or any other mass storage device known for storing instructions on a more permanent basis.

The computer system for the processing unit 114 may include one or more computers or processing units at the same or different locations. When at different locations, the computers may be configured to communicate with one another through a wired and/or wireless network communication system, such as the communication unit 708. The communication unit 708 may include network interface devices (I/F) for wired and wireless connectivity. For example, the communication unit 708 may include a CAT-type interface, USB interface, or SD interface, transceivers for sending and receiving signals using Wi-Fi™; Bluetooth®, or cellular communications for wireless communication, etc. The communication unit 708 can link the processor(s) 702 to a computer network that may in turn be coupled to other processing systems.

The display 710 represents any device equipped to display electronic images and data as described herein. The display 710 may be any of a conventional display device, monitor or screen, such as an organic light-emitting diode (OLED) display, a liquid crystal display (LCD). In some embodiments, the display 710 is a touch-screen display capable of receiving input from one or more fingers of a user. For example, the device 710 may be a capacitive touch-screen display capable of detecting and interpreting multiple points of contact with the display surface.

The input device(s) 712 are any devices for inputting data on the computer system 700. In some embodiments, an input device is a touch-screen display capable of receiving input from one or more fingers of the user. The functionality of the input device(s) 712 and the display 710 may be integrated, and a user of the computer system 700 may interact with the system by contacting a surface of the display 710 using one or more fingers. In other embodiments, an input device is a separate peripheral device or combination of devices. For example, the input device(s) 712 may include a keyboard (e.g., a QWERTY keyboard) and a pointing device (e.g., a mouse or touchpad). The input device(s) 712 may also include a microphone, a web camera, or other similar audio or video capture devices.

The data store 714 can be an information source capable of storing and providing access to data. In the depicted embodiment, the data store 714 is coupled for communication with the components 702, 704, 708, 710, and 712 of the computer system 700 via the bus 716, and coupled, via the processor(s) 702, for communication with the avascular region detection algorithm 706. In some embodiments, the avascular region detection algorithm 706 is configured to manipulate, i.e., store, query, update, and/or delete, data stored in the data store 714 using programmatic operations.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

Furthermore, the description can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The foregoing description of the embodiments of the present subject matter has been presented for the purposes of illustration and description. It is not intended to be exhaustive or to limit the present embodiment of subject matter to the precise form disclosed. Many modifications and variations are possible in light of the above teaching. As will be understood by those familiar with the art, the present subject matter may be embodied in other specific forms without departing from the spirit or essential characteristics thereof. Furthermore, it should be understood that the modules, routines, features, attributes, methodologies and other aspects of the present subject matter can be implemented using hardware, firmware, software, or any combination of the three.

The invention claimed is:

1. A method of characterizing refraction using an ophthalmic imaging system, said method comprising:
   illuminating a region of the retina of an eye along a first illumination path passing through a first location on the pupil of the eye using a light source;
   collecting light returning from the region of the retina on a detector, wherein the returning light travels along a collection path and passes through a second location on the pupil of the eye distinct from the first location;
   determining a shift in the location of the collected light on the detector relative to a predetermined location on the detector, said shift corresponding to the mismatch between the refractions of the ophthalmic imaging system and the eye; and
   storing or displaying the determined shift or a further analysis thereof.

2. The method as recited in claim 1, wherein the light source is scanned and illuminates multiple regions of the retina and the collecting, determining, and storing or displaying steps are repeated for each illuminated region to create a refraction map of the retina.

3. The method as recited in claim 1, wherein the imaging system is a slit-scanning ophthalmoscope that illuminates the region on the retina with a slit-shaped pattern of light.

4. The method as recited in claim 3, further comprising directing the slit shaped pattern of light to different regions of the retina and repeating the collecting, determining, and storing or displaying steps for each illumination region to create a refraction map of the retina.

5. The method as recited in claim 1, wherein the determined shift is used to focus the imaging system.

6. The method as recited in claim 5, wherein the focus of the imaging system is adjusted automatically by the ophthalmic imaging system.

7. The method as recited in claim 1, wherein the determined shift is used to assess the condition of the retina.

8. The method as recited in claim 7, wherein the condition of the retina is one of abnormality of shape or myopia.

9. The method as recited in claim 7, further comprising repeating the illuminating, collecting, determining, storing or displaying steps with a different direction of displacement between the illumination and collection locations on the pupil.

10. The method as recited in claim 1, further comprising illuminating the same region on the retina with a second light source, such that the illumination patterns generated by the two light sources illuminate the region on the retina sequentially and the second light source travels along a second illumination path that passes through the pupil of the eye at a different location than the first illumination path and repeating the collecting, determining, storing or displaying steps for the second illumination and determining the difference in the shifts for the two illuminations.

11. The method as recited in claim 10, wherein the second illumination source is used when the eye has been dilated and further comprising adjusting alignment cues provided to the eye when the second light source is being used.

12. The method as recited in claim 1, wherein the predetermined location on the detector corresponds to a focused condition of the imaging system.

13. A method of evaluating refraction using an ophthalmic imaging system, said method comprising:
   (a) illuminating a first region of the retina of an eye with a first light source along a first illumination path, said first illumination path passing through a first location on the pupil of the eye;
   (b) collecting light returning from the first region of the retina on a detector;
   (c) after completing steps (a) and (b) separately illuminating a second region of the retina with a second light source along a second illumination path, said second illumination path passing through a second location on the pupil of the eye different from the first location on the pupil;
   (d) collecting light returning from the second region of the retina on the detector;
   (e) determining the difference in the shifts in the locations of the collected light on the detector for the two illumination paths;
   (f) storing or displaying the difference in shifts or a further analysis thereof.

14. The method as recited in claim 13, further comprising illuminating different regions of the retina with the first and second light sources and repeating the collecting, determining, and storing or displaying steps for each pair of sequential illuminations.

15. The method as recited in claim 13, wherein the ophthalmic imaging system is a slit-scanning ophthalmoscope that illuminates the regions of the eye with a slit-shaped pattern of light.

16. A method of evaluating refraction using an ophthalmic imaging system, said method comprising:

illuminating a first region of the retina of an eye with a first light source along a first illumination path, said first illumination path passing through a first location on the pupil of the eye;

collecting light returning from the first region of the retina on a detector;

illuminating a second region of the retina with a second light source along a second illumination path, said second illumination path passing through a second location on the pupil of the eye different from the first location on the pupil;

collecting light returning from the second region of the retina on the detector;

determining the difference in the shifts in the locations of the collected light on the detector for the two illumination paths;

storing or displaying the difference in shifts or a further analysis thereof and wherein the method is used to image an eye that has been dilated.

17. The method as recited in claim 13, wherein the difference in shifts is used to focus the instrument and/or to assess the condition of the retina.

18. The method as recited in claim 17, wherein the difference in shifts is used to focus the instrument and the focus of the instrument is adjusted automatically.

19. The method as recited in claim 17, wherein the difference in shifts is used to assess the condition of the retina and the condition of the retina is one of abnormality of shape or myopia.

20. A method of evaluating refraction using an ophthalmic imaging system, said method comprising:

illuminating a first region of the retina of an eye with a first light source along a first illumination path, said first illumination path passing through a first location on the pupil of the eye;

collecting light returning from the first region of the retina on a detector;

illuminating a second region of the retina with a second light source along a second illumination path, said second illumination path passing through a second location on the pupil of the eye different from the first location on the pupil;

collecting light returning from the second region of the retina on the detector;

determining the difference in the shifts in the locations of the collected light on the detector for the two illumination paths;

storing or displaying the difference in shifts or a further analysis thereof and illuminating different regions of the retina with the first and second light sources and repeating the collecting, determining, and storing or displaying steps for each pair of sequential illuminations and wherein the repeated collecting, determining, and storing or displaying steps are performed with a different direction of displacement between the illumination and collection locations on the pupil.

21. The method as recited in claim 20, in which the difference in shifts is used to calculate one of spherical focus, astigmatism and orientation of astigmatism.

22. The method as recited in claim 13, wherein the first and second regions on the retina are the same.

23. The method of claim 1 wherein the detector is a camera.

24. The method of claim 13 wherein the detector is a camera.

* * * * *

UNITED STATES PATENT AND TRADEMARK OFFICE
CERTIFICATE OF CORRECTION

PATENT NO. : 11,395,589 B2
APPLICATION NO. : 16/494016
DATED : July 26, 2022
INVENTOR(S) : Matthew J. Everett et al.

It is certified that error appears in the above-identified patent and that said Letters Patent is hereby corrected as shown below:

On the Title Page

In item (56), in Column 2, under "Other Publications", Line 1, delete "Reporton" and insert -- Report on --.

In item (57), in Column 2, in "Abstract", Lines 1-2, delete "ophthalmo-scopes," and insert -- ophthalmoscopes, --.

On the page 2, in Column 2, under "Other Publications", Line 9, delete "Pumkin," and insert -- Pumpkin, --.

In the Drawings

On sheet 11 of 12, in Figure 7, reference numeral 706, Line 3, delete "Algoirthm" and insert -- Algorithm --.

In the Specification

In Column 4, Line 28, delete "retina" and insert -- retina. --.

Signed and Sealed this
Twenty-fifth Day of October, 2022

Katherine Kelly Vidal
*Director of the United States Patent and Trademark Office*